United States Patent
Raspanti et al.

(10) Patent No.: US 6,399,047 B1
(45) Date of Patent: Jun. 4, 2002

(54) BENZOXAZOLE DERIVATIVES FOR USE IN COSMETIC COMPOSITIONS AND FOR STABILIZING SYNTHETIC POLYMERS

(75) Inventors: Giuseppe Raspanti; Giorgio Zanchi, both of Bergamo (IT)

(73) Assignee: 3V Sigma S.p.A., Milan (IT)

( * ) Notice: Subject to any disclaimer, the term of this patent is extended or adjusted under 35 U.S.C. 154(b) by 0 days.

(21) Appl. No.: 09/777,684

(22) Filed: Feb. 7, 2001

(30) Foreign Application Priority Data

Nov. 2, 2000 (IT) .......................... MI200A226

(51) Int. Cl.⁷ ................................. A61K 7/42
(52) U.S. Cl. ..................... 424/59; 424/401; 424/60; 544/196; 544/197; 544/198
(58) Field of Search ............ 424/401, 59, 60; 544/196, 197, 198

(56) References Cited

FOREIGN PATENT DOCUMENTS

| | | |
|---|---|---|
| EP | 0832642 A2 | 4/1998 |
| IT | 0 832 642 A2 * | 4/1998 |

* cited by examiner

*Primary Examiner*—Jose'G. Dees
*Assistant Examiner*—Konata M. George
(74) *Attorney, Agent, or Firm*—Birch, Stewart, Kolasch & Birch, LLP

(57) ABSTRACT

Compounds of formula (I),

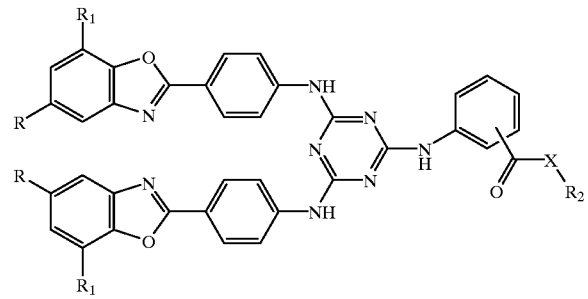

wherein the groups are as defined in the disclosure, as well as the use thereof in cosmetic compositions and in the stabilization of synthetic polymers.

11 Claims, No Drawings

BENZOXAZOLE DERIVATIVES FOR USE IN COSMETIC COMPOSITIONS AND FOR STABILIZING SYNTHETIC POLYMERS

The present invention relates to benzoxazole derivatives and their use in cosmetic compositions and in the stabilization of synthetic polymers.

It is well known that sun radiations ranging from 290 to 400 nm are noxious for the organic materials, among which cutaneous tissue too. In fact, prolonged exposition to sun radiation is considered to be the main cause of the development of degenerative processes and of skin cancer forms. In particular, radiations of wavelength between 290 and 320 nm, so called UV-B radiations, cause erythema and sunburns, whose severity depends on exposure length.

It was ascertained that also the radiations ranging between 320 and 400 nm, so called UV-A, and responsible of skin tanning, can cause alterations and damages in the skin may not be disregarded, such as for example degenerative processes and even cancer forms; especially in case of sensible skins or in case of prolonged exposition to radiation.

It has also been demonstrated that the UV-A radiation other than causing damages to elastin and collagen, whose consequence is ageing of the skin, can also be the cause of a number of phototoxic and photoallergic reactions. Besides, the noxious action of UV-B may be enhanced by the presence of UV-A (see: Willis et al.: Journal of Investigative Dermatology vol. 59, 416, 1072).

By means of the use of particular compounds or of compositions containing these particular compounds, so called sunscreens or UV filters, capable of absorbing, at least partially, UV sunlight radiations, noxious effects on organic materials, in particular on synthetic polymers and on human skin can be prevented or at least attenuate and ageing of the same showed down. As protective agents a number of substances have been studied and experimented and a wide patent literature exists on this matter, wherein compounds belonging to different chemical classes capable of absorbing in the UV zone of sun radiation and particularly that between 290 and 360 nm are proposed.

Many compounds such as for example derivatives of cinnamic acid, 4-aminobenzoic acid, benzylydenecamphor, benzophenone and diphenylcyanoacrylic acid are well known and widely used in cosmetic preparations for the protection from sunburns and erythema due to noxious UV-B radiation.

Until recently the use of sunscreens for the protection from the UV-A radiation was practically unknown, other than some special cases of therapy. But recent studies show that also a continuous and intensive UV-A radiation can cause severe cutaneous damages, especially to persons having very sensible and delicate skin.

For the protection against UV-A, really suitable products are not yet available, even if in the patent literature some compounds have been proposed, but in practice, the outcome of these compounds may not be considered sufficiently positive.

2-Hydroxy-4-methoxybenzophenone is an often used commercial product, whose maximum absorption in the UV-A zone, at about 325 nm, is too low to give an effective protection, moreover its solubility in solvents usually used in cosmetics is very low thus making difficult its handling.

Another compound presently used in practice is a dibenzoylmethane derivative, but not only it is incompatible with many ingredients usually employed for cosmetic compositions, but also has the severe defect of not being sufficiently photostable (Int. J. Cosm. Science 10, 53 1988), therefore the sun formulations containing these compounds may not guarantee a sufficient protection from UV-A since the sunscreens are either too weak (such as the benzophenone derivative) or are degraded too quickly by the radiation itself (such as the dibenzoylmethane derivative).

Better results were obtained with the benzoxazole derivatives disclosed in U.S. Pat. No. 5,744,127.

However, the problems connected with the use of such UV sunscreens, particularly those concerning their solubility in the oily solvents conventionally used in cosmetic formulations, have not been solved.

A high solubility of UV filters in the cosmetic ingredients is, in fact, mandatory for the preparation of formulations having optimal sun protection factors.

DISCLOSURE OF THE INVENTION

It has now surprisingly been found that particular benzoxazole derivatives have such characteristics as to meet the present market requirements. In fact, in addition to good absorption, and therefore high protective efficiency in the zone between 320 and 360 nm, they also show good photostability, wide compatibility with the cosmetic ingredients and high solubility in the solvents usually employed in cosmetic compositions. The compounds according to the present invention have the following formula (I):

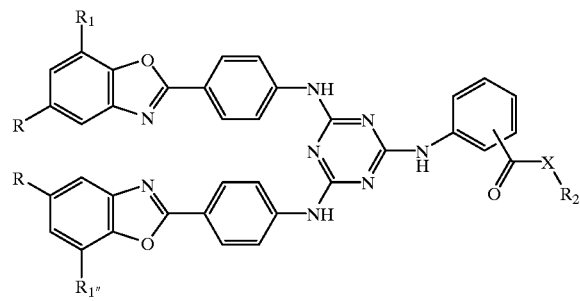

wherein

R and R1, which can be the same or different, are hydrogen, straight or branched C1–C8 alkyl, —OR3 wherein R3 is a C1–C4 alkyl group, —COOR4 wherein R4 is a straight or branched C1–C24 alkyl, a C7–C12 aralkyl or C5–C8 cycloalkyl group or a group of formula (II) or (III):

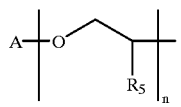

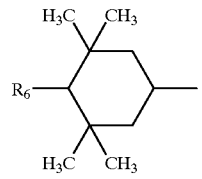

wherein

A is straight or branched C1–C8 alkyl, C5–C8 cycloalkyl, C6–C10 aryl optionally substituted with one or more C1–C4 alkyl, R5 and R6 are independently hydrogen or methyl, n can have values of 1 to 10, R2 is independently straight or branched C1–C18 alkyl, C5–12 cycloalkyl, optionally substituted with 1 to 3 straight or branched C1–C4 alkyl groups; an ammonium group optionally substituted with 1 to 4 C1–C4 alkyl groups or a group of formula (II) or (III) and the —CO—X—R2 moiety can be at the ortho or meta positions, X is oxygen or NH.

A first group of preferred compounds comprises those wherein R and R1 have the meanings defined above and R2 is a straight or branched C1–C18 alkyl group.

A second group of preferred compounds comprises those wherein R and R1 have the meanings defined above and R2 is a group of formula (III).

A third group of preferred compounds comprises those wherein R and R1 have the meanings defined above, R2 is a straight or branched C2–C12 alkyl residue and X is oxygen.

Examples of alkyl groups are methyl, propyl, butyl, hexyl, heptyl, octyl, decyl, dodecyl, pentadecyl, heptadecyl, eicosanyl and the branched isomers thereof, optionally containing oxygen bridges in the form of ether groups. Particularly preferred are 2-octyldodecyl, 2-ethyldecyl, tert-butyl, 2-ethylhexyl, 1,1,3,3-tetramethylbutyl, isobutyl groups.

Examples of aralkyl groups are benzyl, phenylethyl, phenylpropyl, phenylhexyl, naphthylmethyl, naphthylethyl and the isomers thereof. Aryl is phenyl or naphthyl, any substitutions with alkyl groups, such as methyl, ethyl, isopropyl, tert-butyl, can be at the ortho, meta and para positions and on the naphthyl fused ring.

Examples of cycloalkyl groups are cyclopentyl, cyclohexyl, cyclooctyl.

The compounds according to the present invention absorb UV radiations intensely and particularly in the UV-A range, therefore small amounts of these compounds are sufficient to obtain cosmetic compositions with high SPF (Sun Protecting factor). SPF is directly related to the specific extinction and is determined in vivo on man or according to a in vitro method as described by B. Diffey J. Robson in J. Soc. Cosmet. Chem. 40, 127–133 (1989).

Moreover, the compounds of formula (I), also depending on the $R_2$–$R_4$ substituents, show a wide absorption, which is not only confined in the UV-A range, but also extended to the UV-B range. Therefore, they can provide protection against both UV-A and UV-B radiations.

It is therefore a further object of the invention the use of the compounds of formula (I) as sunscreens in cosmetic compositions and as photostabilizing agents for the protection of synthetic polymers.

In particular, it is an object of the present invention the use of the compounds of formula (I) as sunscreens in the cosmetic treatment of the skin.

A further object of the present invention are cosmetic compositions containing at least a compound of formula (I).

The compounds according to the present invention can be prepared by reacting a compound of formula (IV):

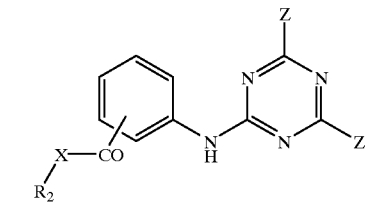

with compounds of formula (V):

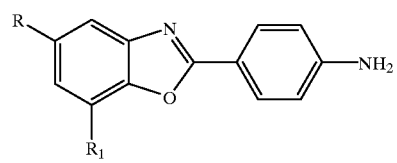

wherein R, R1, R2 and X have the meanings defined above, z is bromine or preferably chlorine.

Alternatively, a compound of formula (VI):

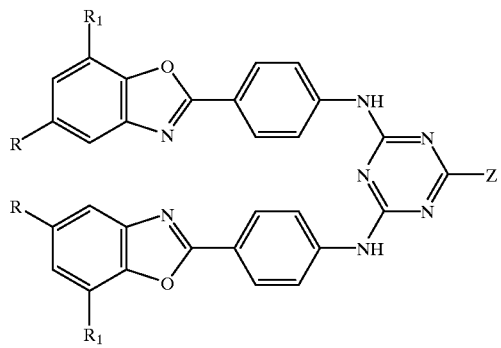

is reacted with a compound of formula (VII)

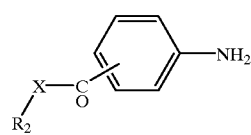

wherein R, R1, R2, Z and X are as defined in formula (I).

The intermediates of formula (IV), (V), (VI) and (VII) are prepared according to known procedures.

The intermediates of formula (IV) and (VI), before the subsequent reaction with the compounds of formula (V) and (VII), may be isolated and purified or, more easily, they are reacted as raw materials, considering them as the first step of a multistep synthesis.

The reaction of the trichlorotriazine to substitute the three chlorine atoms with amino groups, which can be the same or different, is well-known and thoroughly described in literature, especially that relating to some classes of dyes and optical brighteners.

The reaction between the compounds of formula (IV) and (VI) and between those of formula (V) and (VII) is carried out at a temperature ranging between 50 and 200° C., in suitable solvents, such as acetonitrile, ketones such as acetone, methylethyl ketone, ethers such as diisopropyl ether, tetrahydrofuran, dioxane, aliphatic or aromatic hydrocarbons, such as hexane, octane, cyclohexane, benzene, toluene, xylene or mixtures thereof, optionally in the presence of an acid acceptor, such as alkali or alkaline-earth hydroxide, alkali metal carbonates or bicarbonates.

The final compounds are isolated and purified according to usual methods.

According to the present invention, the compounds of formula (I) are useful as sunscreens. Their protective activity on the skin from sun radiation is carried out by applying a suitable amount on the part of the skin which is exposed to the radiations.

Suitable amounts for the application can be determined by those skilled in the art, depending on the specific extinction coefficient $E^1$ of the compound of formula (I). Said coefficient is an index of the protection efficacy.

A further object of the present invention is represented by cosmetic compositions containing an effective amount of at least a compound of formula (I) as sunscreen in combination with conventional carriers and excipients.

Said compositions can be of different types, for example in the form of solutions, lotions, water-in-oil or oil-in-water emulsions; or also in the form of gels, lipsticks, sprays.

The compositions according to the present invention can be prepared by admixing conventional ingredients, carriers and excipients such as oils, fats, emollients, hydrating agents, moisturizing agents, softening agents, preservatives, surfactants, thickening agents, antifoam agents, perfumes, pigments, dyes and the like such as alcohols, polyols, electrolytes, silicone derivatives. The most commonly used solvents are triglycerides of capric or caprylic acid, castor oil, esters of fatty acids with isopropanol, propylene glycol, glycerin, propylene glycol monomethyl or monoethyl or monobutyl ether, dioctyl malate.

The present invention also comprises the protection of cosmetic compositions from UV radiation by using the compounds of formula (I), in case the cosmetic ingredients are liable to undergo unwanted degradation or colouring due to light, such as hair shampoos and lacquers, hairdress lotions, hair-dye compositions, make-up formulations, such as nail lacquers, foundations, lipsticks.

Preferred cosmetic compositions are those for the protection of the skin from sun radiations.

The cosmetic compositions of the present invention can contain one or more compounds of formula (I), in an amount comprised from 0.1 to 20%, preferably from 0.5 to 15% by weight with respect to the total weight of the composition.

According to the invention, in addition to the compounds of formula (I), also other sunscreens can be added, particularly those having a maximum absorption comprised from 290 to 320 nm.

In such a manner, a protection both against UV-A and UV-B radiations can be obtained. Well-known sunscreens, which can be combined with the compounds of formula (I) are for example:

3-(4-methylbenzylydene)-camphor; 2-ethylhexyl-(4-dimethyl-amino)benzoate; 2-ethylhexyl-4-methoxycinnamate menthyl salicylate; 2-hydroxy-4-methoxy-benzophenone; 2,4,6-trianilino-(p-carbo-2-ethyl-hexyloxy)-1,3,5-triazine; 4-(1,1-dimethylethyl)-4'-methoxydibenzoyl-methane; triazine derivatives disclosed in U.S. Pat. No. 5,346,691; 2-ethylhexyl-2-cyano -3,3-diphenylacrylate; 2-phenyl-benzimidazol-5-sulfonic acid, 2-hydroxy -4-methoxy-benzophenone-5-sulfonic acid or 1,4-di-(3-methylbenzylidenecamphor) -10-sulfonic salts.

The application of the sunscreens according to the present invention can be carried out by means of cosmetic compositions containing one or more compounds of formula (I), optionally combined with one or more well-known sunscreens, such as those cited above.

It is understood that the above list of sunscreens which may be combined with the sunscreens of formula (I) is only given by way of example, and it is not intended to be limited.

The cosmetic compositions containing the compounds of formula (I) of the invention are used for the treatment of skin, hair or for cosmetic make-up.

In another aspect, the present invention also provides the use of compounds of formula (I) for the protection of synthetic polymers. According to the present invention, polymeric materials, which can be protected from UV radiation, include polyethylene, polypropylene, polystyrene, polybutadiene, polyisoprene and their copolymers, polyvinyl acetate and its copolymers, particularly with polyethylene, polyesters such as polyethylene terephthalate, polyamides such as Nylon 6 and Nylon 6,6, polyurethanes, polyacrylates, polymethacrylates, polyvinyl chloride.

The compounds of formula (I) can be incorporated in polymers to be stabilized by means of any known method for mixing or blending additives to polymeric materials; for example, they can be mixed with the polymer in a suitable blender or mixer, or added in the form of solution or suspension in a suitable solvent such as methanol, ethanol, acetone, chloroform, then removing the solvent after mixing with the polymer, which can be in the form of powder, granulate or suspension or finally can be added to the polymer during the preparation of the same, for example in the last preparation step.

The compounds of formula (I) can be also used in combination with other stabilizing agents and additives generally used for polymers, such as for example phenol-based antioxydants, phosphites, hindered amines and particularly those containing in their structure the 2,2,6,6-tetramethylpiperidine group, other types of UV-absorbers based on benzotriazoles or benzophenones, plastifiers, lubricants, flame retardants, titanium oxide.

The amount of compounds of formula (I) necessary to an effective stabilization of the polymer depends on different factors, such as the kind and the characteristics of the polymer, the use to which it is intended, the intensity of the radiation, the duration of exposure and the presence, if any, of other stabilizing agents.

Generally, an amount comprised from 0.01 to 5% by weight of the polymer, preferably from 0.05 to 2% will be sufficient. The following examples further illustrate the invention.

EXAMPLE 1

109 g of o-aminophenol in 1000 ml of xylene were added with 185.5 g of p-nitrobenzoyl chloride. The resulting suspension was slowly heated to 130° C. The formed hydrochloric acid was neutralized by sending it to a NaOH solution.

After HCL evolution ceased (after about 1 hour), 9.5 g of p-toluenesulfonic acid were added to the reaction mixture, stirring under reflux for about 3 hours, while azeotropically distilling off and collecting the reaction water. After cooling to 60° C., filtering and repeatedly washing with acetone and drying, 225 g of 2-(p-nitrophenyl)-benzoxazole were obtained as a cream colored substance. This was loaded, together with 1,400 ml of ethylene glycol monomethyl ether and 2 g of 5% Pt/C in autoclave, washed 2–3 times with nitrogen and then with hydrogen.

Subsequently, hydrogen was introduced to reach a pressure of 10 atm and temperature was slowly raised to 90° C., while stirring. Stirring was continued at 80–90° C. until hydrogen absorption ceased, keeping the pressure between 10 and 15 atm.

After cooling, overpressure was discharged, and the reaction mixture was washed with nitrogen. The catalyst was filtered off, and the resulting solution was vacuum-evaporated to dryness. The residue was crystallized from toluene with addition of decoloring earth. 170 g of 2-(p-aminophenyl) -benzoxazole with m.p. 176–179° C. were obtained.

EXAMPLES 2–4

Operating as described in Example 1, the benzoxazoles of formula (V) listed in table 1, were prepared.

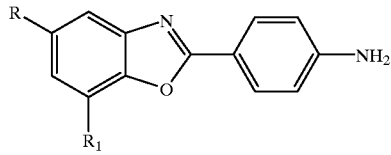

TABLE 1

| Example | R | R1 | m.p. ° C. |
| --- | --- | --- | --- |
| 2 | (CH3)3C— | H | 167–168 |
| 3 | (CH3)3C— | (CH3)3C— | 168–169 |
| 4 | CH3—CH2—(CH3)2-C— | H | 153–154 |

EXAMPLE 5

A solution of 46.2 g of trichlorotriazine in 450 ml of acetone, containing 22 g of sodium bicarbonate, cooled to 0° C., was slowly added with 64.7 g of 2-ethylhexylanthranylate, keeping the temperature from 0 to 5° C. by cooling. When the addition was over, the mixture was stirred for a further ½ hour, then added with 175 ml of water and stirred for a further hour, keeping the temperature between 0 and 5° C. The formed precipitate was filtered, thoroughly washed with water, then with acetone and finally dried. 84 g of a white product were obtained, m.p. 136–138° C., with the following formula:

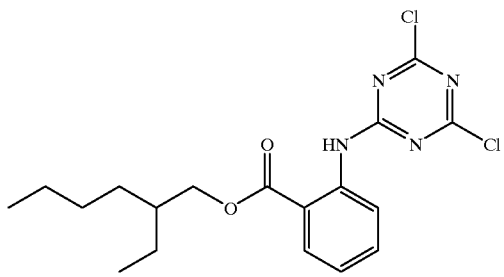

EXAMPLES 6–8

Operating as described in Example 5, the compounds listed in Table 2 prepared:

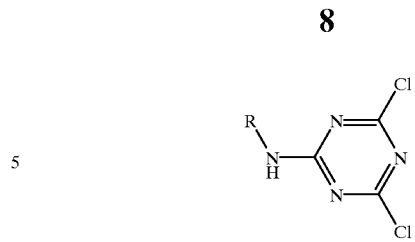

TABLE 2

| Example | R | m.p./° C. |
| --- | --- | --- |
| 6 | ![structure] | 151–152 |
| 7 | ![structure] | 206.5–208 |
| 8 | ![structure] | 195.5–196.5 |

EXAMPLE 9

9.93 g of the dichlorotriazine derivative of Example 6 and 10.82 g of the benzoxazole derivative of Example 1 in 100 ml of xylene were stirred under reflux for 8 hours in nitrogen stream. The formed hydrochloric acid was sent to a diluted NaOH solution. Xylene was distilled off and the residue was suspended in acetonitrile, stirred, filtered and washed with dry acetonitrile. 14.8 g of a product were obtained, m.p. 179.5–181° C., and E' 1402 at 336 nm, with the following formula:

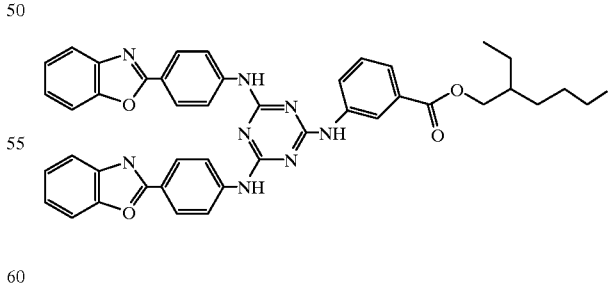

EXAMPLES 10–14

Operating as described in Example 9, by reacting, compounds of formula (IV) with those of formula (V), the compounds of formula (I) listed in Table 3 were obtained.

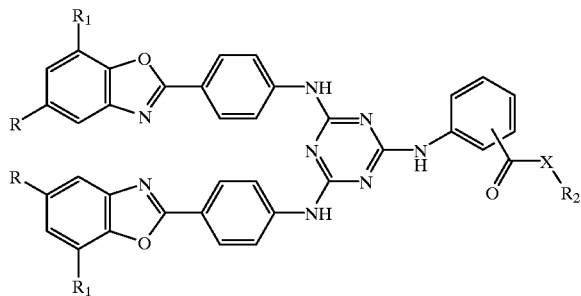

-continued

| | |
|---|---|
| Perfume | 0.3 g |
| Distilled water q.s. to | 100.0 g |

The fatty phase was heated to 80–90° C., the sunscreen of example 10 and 2-ethylhexyl-4-dimethylaminobenzoate were added, then the mixture was added to water, containing the hydrosoluble compounds, heated to 80–90° C. Warm-stirring was continued for 15–20 minutes. After slow cooling, perfume was added.

TABLE 3

| Ex. | R | R1 | R2 | X | m.p./° C. | E' | nm |
|---|---|---|---|---|---|---|---|
| 10 | (CH3)3— | H | 2-ethylhexyl 2-methylbenzoate | O | 137.5–139 | 1352 | 337 |
| 11 | (CH3)3— | H | 2-ethylhexyl 3-methylbenzoate | O | 132.5–135 | 1259 | 337 |
| 12 | (CH3)3— | H | N-tert-butyl 3-methylbenzamide | NH | 193–194 | 1280 | 337 |
| 13 | C2H5C(CH3)3— | H | N-tert-butyl 3-methylbenzamide | NH | 179.5–181 | 1276 | 338 |
| 14 | (CH3)3— | (CH3)3— | neopentyl 2-methylbenzoate | O | 139.5–141.5 | 1158 | 336 |

Example A

Sun Cream

| | |
|---|---|
| Polyglycol (Arlacel 165 ICI) | 2.0 g |
| Glycerin monostearate | 4.0 g |
| Benzoate of C12–C15 alcohol | 5.0 g |
| Cetylstearyl alcohol | 3.0 g |
| Myristic alcohol with 3 mols of propylene oxide (Witcamol APM-Witco) | 29.0 g |
| Compound of example 10 | 2.0 g |
| 2-Ethylhexyl-4-dimethylaminobenzoate | 2.5 g |

Example B

Sun-milk

| | |
|---|---|
| Fatty acid triglycerids | 20.0 g |
| Cetystearyl alcohol | 2.0 g |
| Lanolin | 4.0 g |
| Cetyl alcohol | 2.0 g |
| Siliconic oil | 0.4 g |
| Compound of example 12 | 3.5 g |
| Abiol (preservative by 3V SIGMA) | 0.2 g |
| Synthalen M (thickening agent by 3V SIGMA) | 0.1 g |

-continued

|  |  |
|---|---|
| Triethanolamine | 0.15 g |
| Perfume | 0.3 g |
| Distilled water q.s. to | 100.0 g |

The preparation was carried out as in Example A.

Example C

Day Cream

|  |  |
|---|---|
| C8–C12 acid triglycerids | 29.8 g |
| Glycerol monostearate | 7.0 g |
| Stearic acid | 2.0 g |
| Lanolin | 4.0 g |
| Preservative | 0.2 g |
| Compound of example 11 | 2.0 g |
| Propylene glycol | 2.5 g |
| Triethanolamine | 0.5 g |
| Perfume | 0.3 g |
| Distilled water q.s. to | 100.0 g |

The preparation was carried out as in Example A.

Example D

Alcoholic Gel

|  |  |
|---|---|
| Propylene glycol | 25.0 g |
| Ethanol | 25.0 g |
| Synthalen M (thickening agent by 3V SIGMA) | 0.6 g |
| Compound of example 14 | 2.5 g |
| Triethanolamine | 0.3 g |
| Preservative | 0.3 g |
| Perfume | 0.3 g |
| Distilled water q.s. to | 100.0 g |

Synthalen M was dispersed in water, then triethanolamine, preservative, propylene glycol and ethanol mixture, in which the compound of example 14 had previously been dissolved, were added, followed by perfume.

Example E

Lipstick

A base mixture was first prepared, consisting of:

|  |  |
|---|---|
| Beeswax | 13.0 g |
| Carnauba wax | 7.5 g |
| Lanolin | 5.0 g |
| Isopropyl myristate | 8.0 g |
| Mineral oil | 3.0 g |
| Castor oil | 63.5 g |

85 g of this mixture were warmed up to melt, then the molten mass was added with 5 g of compound of example 9 and 4 g of compound of example 44 in table 3 of U.S. Pat. No. 5,346,691, as well as perfume, flavors and dyes, then it was diluted to 1000 g with castor oil and cooled to room temperature.

Example F 1000 g of low density polyethylene (Riblene EF 2100 R Enichem), 2 g of n-octadecyl-3-(3,5-of-terbutyl-4-hydroxyphenyl) propionate, 1 g of calcium stearate and 0.3 g of a compound of formula (I) were homogeneously mixed. The obtained mixtures were extruded at 190° C. and transformed into granules. From these, by pressing at 200° C., films of 0.2 nm were obtained.

Samples of these films were subjected to UV radiations in a Weatheromether WOM Ci-65 at a black panel temperature of 63° C. In the irradiated samples, the increase of the carbonylic band at 5.85 nm in infrared field was measured and T-0.1, i.e. the time necessary to achieve an increase of 0.1 of the carbonylic band was determined and compared with a film which did not contain stabilizing agents of formula (I). The results are reported in the Table 4.

TABLE 4

| Stabilizing agent | T 0.1 (hours) |
|---|---|
| Without stabilizing agent | 320 |
| Compound of example 9 | 1140 |
| Compound of example 11 | 1030 |
| Compound of example 12 | 1210 |

What is claimed is:
1. Compounds of formula (I)

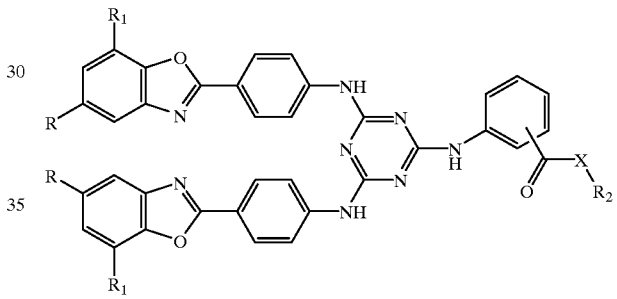

I wherein
R and R1, which can be the same or different, are hydrogen, straight or branched C1–C8 alkyl, —OR3 wherein R3 is a C1–C4 alkyl group, —COOR4 wherein R4 is a straight or branched C1–C24 alkyl, a C7–C12 aralkyl or C5–C8 cycloalkyl group or a group of formula (II) or (III):

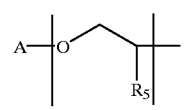

II

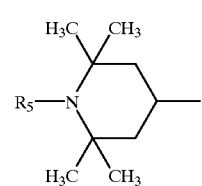

III wherein
A is straight or branched C1–C8 alkyl, C5–C8 cycloalkyl, C6–C10 aryl optionally substituted with one or more C1–C4 alkyl, R5 and R6 are independently hydrogen or methyl, n is values of 1 to 10, R2 is independently straight or branched C1–C18 alkyl, C5–12 cycloalkyl, optionally substituted with 1 to 3 straight or branched C1–C4 alkyl groups; an ammonium group optionally substituted with 1 to 4 C1–C4 alkyl groups or a group of formula (II) or (III) and the —CO—X—R2 moiety can be at the ortho or meta positions, X is oxygen or NH.

2. Compounds as claimed in claim 1, wherein R, R1 and X, have the meanings defined above and R2 is a straight or branched C1–C18 alkyl group.

3. Compounds as claimed in claim 1, wherein R, R1 and X have the meanings defined above and R2 is a group of formula (II).

4. Compounds as claimed in claim 1, wherein R, R1 and X have the meanings defined above, and R2 is a group of formula (III).

5. Compounds as claimed in claim 1, wherein R and R1 have the meanings defined above, R2 is a straight or branched C2–C12 alkyl group and X is oxygen.

6. A method for protecting cosmetic compositions from sunlight UV radiation-induced degradation, comprising adding to said compositions an effective amount of at least one compound of any one of claims 1–4, optionally in combination with other known stabilizing agents.

7. A method for stabilizing synthetic polymers to sunlight UV radiation-induced degradation, comprising adding to said compositions an effective amount of at least one compound of any one of claims 1–4, optionally in combination with other known stabilizing agents and additives for polymers.

8. Cosmetic compositions containing one or more compounds of any one of claims 1–4, in amounts ranging from 0.5 to 10% by weight with respect to the composition.

9. Cosmetic compositions containing one or more compounds of any one of claims 1–4, in admixture with other sunscreens.

10. Compositions of synthetic polymers containing one or more compounds of any one of claims 1–4, in amounts of 0.05–5% with respect to the polymers, and optionally other conventional excipients.

11. Cosmetic compositions as in claim 9, in admixture with UV-B suncreens.

* * * * *

UNITED STATES PATENT AND TRADEMARK OFFICE
CERTIFICATE OF CORRECTION

PATENT NO.    : 6,399,047 B1
DATED         : June 4, 2002
INVENTOR(S)   : Giuseppe Raspanti et al.

It is certified that error appears in the above-identified patent and that said Letters Patent is hereby corrected as shown below:

<u>Title page,</u>
Item [30], Foreign Application Priority Data, please correct the priority date from "Nov. 2, 2000" to -- Feb. 11, 2000 --.

Signed and Sealed this

Twenty-fifth Day of March, 2003

JAMES E. ROGAN
*Director of the United States Patent and Trademark Office*